United States Patent [19]

Stem et al.

[11] Patent Number: 4,982,048
[45] Date of Patent: * Jan. 1, 1991

[54] ISOMERIZATION PROCESS WITH PRELIMINARY NORMAL PARAFFIN AND MONO-METHYL PARAFFIN FEED CAPTURE STEP

[75] Inventors: Stephen C. Stem, Houston; Wayne E. Evans, Richmond, both of Tex.

[73] Assignee: Shell Oil Company, Houston, Tex.

[*] Notice: The portion of the term of this patent subsequent to Feb. 14, 2006 has been disclaimed.

[21] Appl. No.: 315,058

[22] Filed: Feb. 24, 1989

[51] Int. Cl.$^5$ .................................................. C07C 5/13
[52] U.S. Cl. ...................................... 585/751; 585/738; 585/820; 585/822; 585/737; 585/734; 208/310.2
[58] Field of Search ........................... 208/310, 310.2; 585/738, 820, 822, 737, 734, 751

[56] References Cited

U.S. PATENT DOCUMENTS

| | | | |
|---|---|---|---|
| 3,755,144 | 8/1973 | Asselin | 208/95 |
| 3,836,455 | 9/1974 | Blytas | 208/310 |
| 4,176,053 | 11/1979 | Holcombe | 208/310 |
| 4,210,771 | 7/1980 | Holcombe | 585/701 |
| 4,251,499 | 2/1981 | Nanne et al. | 423/329 |
| 4,476,345 | 10/1984 | Gray, Jr. et al. | 585/820 |

FOREIGN PATENT DOCUMENTS 876730 9/1961 United Kingdom .

Primary Examiner—Patrick P. Garvin
Assistant Examiner—E. D. Irzinski

Attorney, Agent, or Firm—Kimbley L. Muller

[57] ABSTRACT

This invention relates to a process for increasing the octane of a refinery gasoline pool by segregating components of a feed stream to increase the value of select components by isomerization and to prevent isomerization of other components already having a high octane value. The preferred feed stream of this process comprises di-branched paraffins, mono-methyl-branched paraffins and normal paraffins. Two or more different separatory sieves are used prior to isomerization. A first separatory shape-selective molecular sieve has a pore size of 4.5×4.5A or smaller to adsorb normal paraffins. A second separatory shape-selective molecular sieve has a pore size of 5.5×5.5 to 4.5×4.5A but excluding 4.5×4.5A. These sieves may be situated in a series flow arrangement. Normal paraffins are adsorbed by the first sieve. Mono-methyl-branched paraffins are adsorbed by the second sieve. The paraffins captured by both sieves are desorbed to form an isomerization zone feed stream which is isomerized to produce additional di-methyl branched paraffins. The isomerization zone effluent stream can undergo further separation to provide a recycle stream comprising normal paraffins or normal paraffins and mono-methyl-branched paraffins in addition to an isomerate stream comprising di-branched paraffins. The separation zone located on the feed stream is exemplified by a first shape-selective molecular sieve comprising a calcium-5A aluminosilicate and a second separatory shape-selective sieve comprising a ferrierate aluminosilicate molecular sieve.

55 Claims, 7 Drawing Sheets

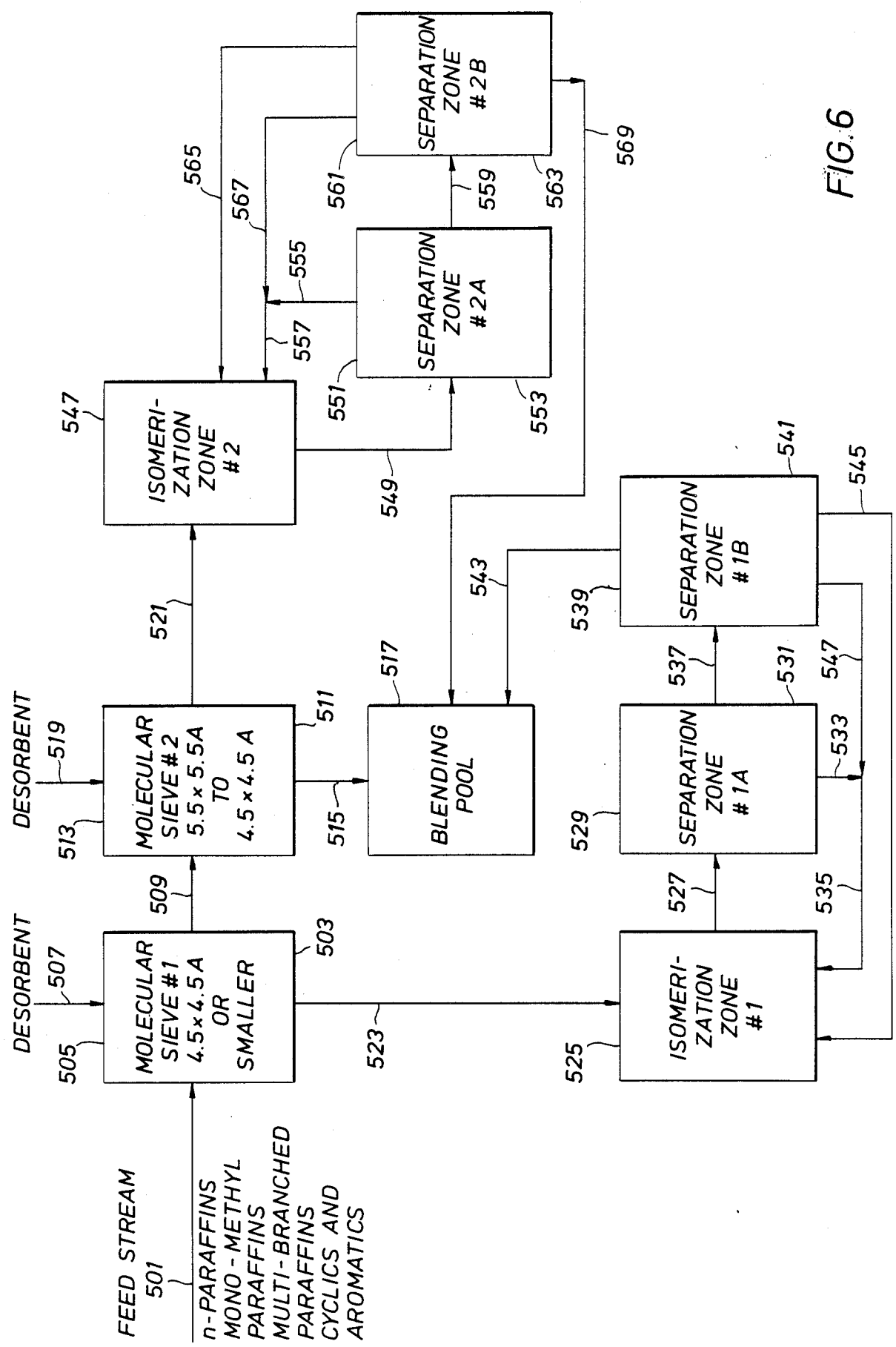

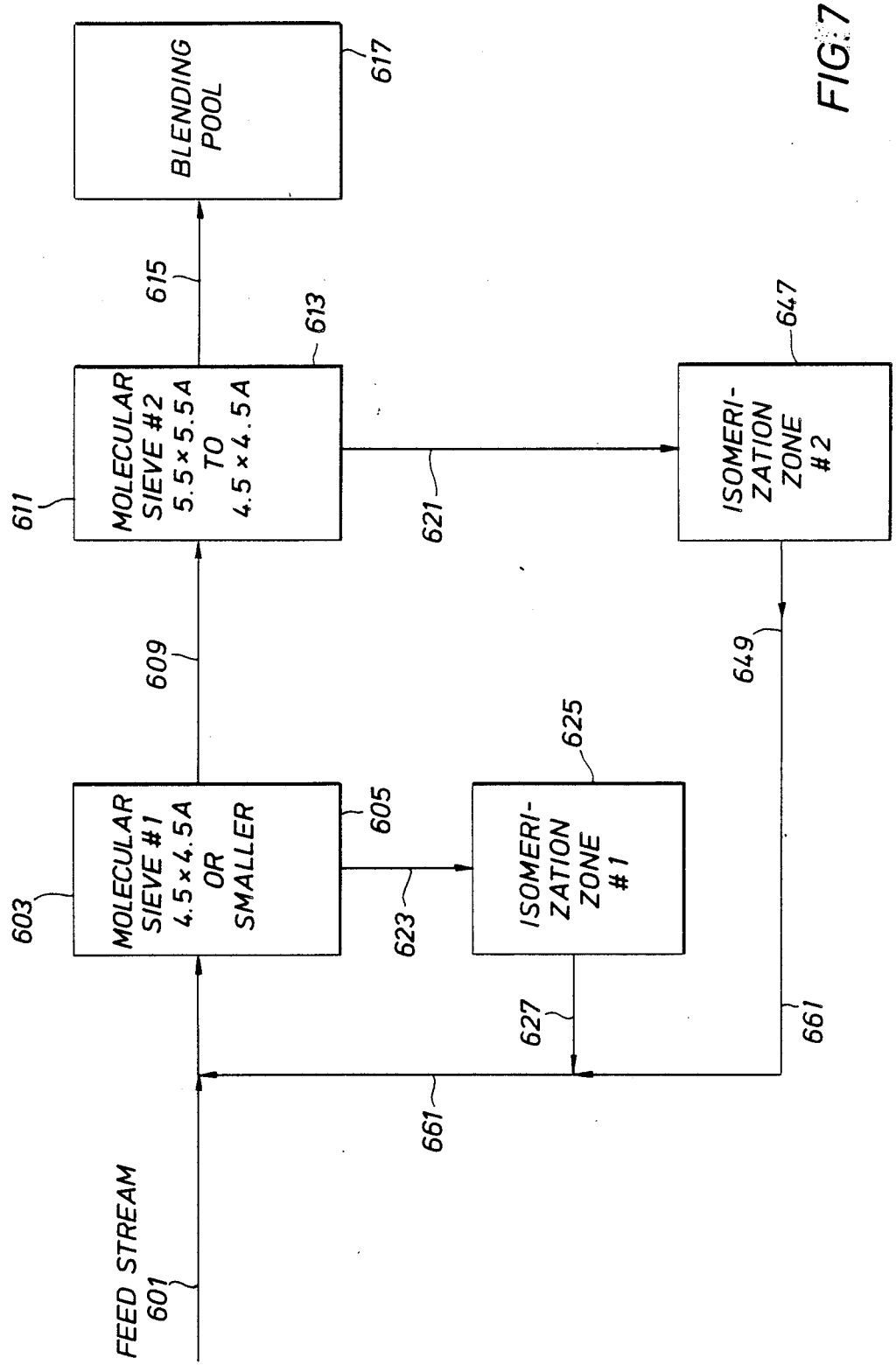

ISOMERIZATION PROCESS WITH PRELIMINARY NORMAL PARAFFIN AND MONO-METHYL PARAFFIN FEED CAPTURE STEP

FIELD OF THE INVENTION

This invention relates to a process which ultimately enhances the octane of a refinery gasoline blending pool. The octane is increased by the use of a select feed pretreatment preceding isomerization. This select pretreatment enables the segregation of said feed into a portion which is increased in value by isomerization from that portion which would be diminished in value by isomerization. This segregation ultimately results in a greater proportion of di-methyl-branched or multi-branched paraffins in the refinery gasoline pool while reducing the proportion of mono-methyl-branched paraffins. As a corollary, the field of this invention is concerned with the development of a multiple pre-isomerization sieve to selectively preserve high octane products while maximizing the quantity of normal and mono-methyl-branched paraffins which are subject to isomerization.

As a result of pollution and environmental problems, retail gasolines in the United States eventually will have a phase-down lead content. Maintenance of high octane gasolines by methods other than lead addition is of continuing interest to U.S. refiners. Two major techniques are available to acquire high octane gasoline pools without lead addition. First, hydrocarbons can be reformed in the presence of a reforming catalyst, such as a platinum rhenium catalyst, to a high octane gasoline. Second normal paraffins can be isomerized to branched paraffins which possess higher octane qualities. This invention concerns the latter of these two processes and is an improvement over standard isomerization processes. The process of this invention supplies a unique pre-isomerization separation step to maximize the effectiveness of the isomerization while preserving that portion of the feed stream which would be diminished in value by isomerization. This is accomplished without the expense of additional hydrocarbon consumption.

From the standpoint of increasing octane, it is desirable that hydrocarbons in gasoline have maximum branching. For example, methylpentanes have lower octane ratings than do dimethylbutanes, thus in an isomerization process it is beneficial to maximize the content of dimethylbutanes (di-branched paraffins) at the expense of methylpentanes (mono-methyl-paraffins). Applicants have discovered that a means to accomplish this goal is to formulate and develop an ideal pre-isomerization separation step using a multiple number of different shape selective molecular sieves. The overall combined product stream of this isomerization process contains an increased amount of dimethylbutanes, the most highly branched and highest octane of the $C_6$ saturates. This results in a direct octane enhancement to the resultant gasoline blending pool. In refineries which restrict production of gasoline due to octane limitations, this octane enhancement can permit increased gasoline production as well.

BACKGROUND OF THE INVENTION

Pertinent areas of the classification manual concerned with this type of invention are, among others, Class 208, Subclass 310 and Class 585, Subclasses 820, 701 and 738.

In Gray Jr. et al, U.S. Pat. No. 4,476,345, an invention is disclosed in which a portion of one of the product streams in an isomerization process is used to wash a recycle gas stream to improve the quality of the isomerate products. The molecular sieve adsorbent of Gray is one which can be naturally occurring or synthetically produced comprising a three-dimensional crystalline-zeolitic aluminosilicate which will selectively, on the basis of molecular size of the pores, adsorb normal paraffins from the isomerized product from branched chained and/or cyclic paraffins. The molecular sieves have pore diameters of about 5A and are exemplified by a calcium 5A zeolite which exhibits pore diameters ranging from about 3 to about 5 Angstroms.

The Gray et al disclosure is an improvement upon an isomerization process as taught in Holcombe, U.S. Pat. No. 4,210,771. This is a process for the virtual complete isomerization of normal paraffin hydrocarbons in a feed stream consisting essentially of mixed normal and branched hydrocarbons, where the feed stream is passed first through an isomerization reactor and the products derived therefrom are passed to an adsorption section which separates normal from branched paraffins to form an isomerate having both di- and mono-branched paraffins. A recycle stream comprising nearly pure normal paraffins is usually recycled to exhaustion. Other disclosures which may be commensurate with Holcombe comprise U.K. Pat. No. 876,730 and U.S. Pat. No. 3,755,144 issued to Asselin.

The zeolite molecular sieve employed in Gray et al and Holcombe may be selected from any adsorbent which selectively adsorbs normal paraffins based on the molecular pore size of the aluminosilicate. Particularly suitable zeolites of this type are calcium exchanged zeolite 5-A. Naturally occurring zeolite molecular sieves which could be substituted for calcium 5-A zeolite include chabazite and erionite. The particular flow scheme of adsorption as taught by Holcombe '771 is herein incorporated by reference to show an operable multiple zeolitic molecular sieve absorption means, to achieve proper adsorption-fill and desorption-purge. The Holcombe patent is completely silent as to arrangements of multiple number of different sieves which ma be present in the absorption separation technique. In fact, in the drawing of Holcombe, the adsorption bed systems, 44, 46, 48, and 50, are all comprised of calcium 5A zeolite in the form of 1/16-inch cylindrical pellets. Branched paraffins, whether they be mono- or di-branched, flow through the adsorption bed while unbranched normal paraffins are adsorbed. After a purge of the adsorbed normal paraffins from the zeolite molecular sieve, the recycle stream is comprised nearly entirely of normal paraffins and recycle hydrogen. This is mixed with the incoming feed before charge to the isomerization zone. The placement of these types of molecular sieves upstream of isomerization will result in only normal paraffins being passed to the isomerization zone while mono-methyl-branched paraffins, in admixture with the more desirable di-branched paraffins, will not be captured and, therefore, will not be further isomerized into the more valuable di-branched paraffins.

A second Holcombe patent, U.S. Pat. No. 4,176,053, discusses a normal paraffin-isomerization separation process. By this technique, normal paraffins are isolated from a feedstock mixture comprising normal and branched paraffins at super atmospheric pressures using an adsorption system comprising at least four fixed adsorbent beds containing a calcium 5A molecular sieve. A stream is formed comprising vapor from void space purgings of the adsorbent and feedstock containing iso-paraffins and normal paraffins. The molecular sieve employed to separate normal paraffins from said stream is selected to adsorb only normal paraffins from a mixture of branched, cyclic and normal hydrocarbons.

In U.S. Pat. No. 3,836,455 issued to Blytas, the separation of methylpentane and 2,2-dimethylbutane (as contrasted with 2,3-dimethylbutane of the instant invention) is accomplished using an offretite zeolite. U.S. Pat. No. 4,251,499 issued to Nanne et al teaches that ferrierite sieves are effective for dividing substantially unbranched structures (n-paraffins) from mixtures of same with branched structures (both mono-methyl and di-branched paraffins). Such was the state of the art in 1981 although the instant invention has shown that this teaching is no longer accurate in regard to the adsorption capacity of ferrierite aluminosilicates as defined herein.

These patents teach that it is most advantageous to recycle normal paraffins to thereby isomerize the same to the isomerate components comprising mono-methyl-branched paraffins and di-branched paraffins. These disclosures suggest that the isomerate will have a certain quantity of mono-methyl-branched paraffins derived from the isomerization zone. These mono-methyl-branched paraffins will have an inherently lower octane value than the di-branched paraffins whether or not they are mixed with the more preferred di-branched paraffins before or after isomerization.

In contrast, applicants have discovered a new and more efficient isomerization process utilizing a multiple number of preisomerization molecular sieve whereby both normal paraffins and mono-methyl-branched paraffins are passed to isomerization with little or no presence of di-branched paraffins. Using the specific multiple pre-isomerization molecular sieves separation technique of this process in either discrete or stacked bed configuration, mono-methyl-branched paraffins are diminished in the refinery gasoline pool while di-branched paraffins or multi-branched paraffins ar both preserved and produced. In other words this process increases the degree of branching in the ultimate refinery gasoline pool by improving the effectiveness of the isomerization step.

OBJECTS AND EMBODIMENTS OF THE INVENTION

An object of this invention is to provide a unique isomerization process which will preserve the already high octane quality of select constituents of the feed prior to conversion of the other remaining paraffinic material to high octane quality isomerate.

Another object of this invention is to provide a unique multiple separatory sieve sequence to pretreat an isomerization zone feed stream to preserve (before isomerization) constituents within said feed, such as aromatics, naphthenes, and di-branched paraffins, which would be diminished in value if they were passed to isomerization.

Another object of this invention is to provide a unique isomerization process whereby a feed stream to an isomerization zone will contain both normal and mono-methyl-branched paraffins but essentially exclude multi-branched paraffins, cyclic paraffins and aromatics, wherein the normal paraffins are isomerized to mono-methyl-branched and di-methyl-branched paraffins and wherein the mono-methyl-branched paraffins are isomerized to di-methyl-branched paraffins.

Another object of this invention is to provide a unique preliminary multiple molecular sieve system upstream of an isomerization zone to insure maximum conversion to di-branched paraffin from normal and mono-methyl paraffins in the isomerization zone.

Yet another object of this invention is to provide a process step whereby 2,3-dimethylbutane can be removed from a mixture containing 2,3-dimethylbutane, normal hexane, and mixtures of methyl pentanes to segregate the 2,3-di-branched paraffins while allowing the normal hexane and methyl pentanes to be isomerized to methyl pentanes and 2,3-dimethylbutane.

One embodiment of this invention resides in a process for the isomerization of paraffins from a mixed hydrocarbon stream comprising normal paraffins, mono-methyl-branched paraffins, and di-methyl-branched paraffins, said process comprising passing said mixed hydrocarbon stream to a first feed separaton zone comprising a first shape-selective separatory molecular sieve having a pore size of 4.5 $\times$ 4.5A or smaller, said pore size being sufficient to permit entry of said normal paraffins but restrictive to prohibit entry of mono-methyl paraffins and di-branched paraffins and to produce a mixed hydrocarbon stream comprising said mono-methyl paraffins and di-branched paraffins, passing said mixed hydrocarbon stream to a second feed separation zone comprising a second shape-selective separatory molecular sieve having a pore size intermediate 5.5$\times$5.5 to 4.5$\times$4.5A and excluding 4.5$\times$4.5A, said pore size being sufficient to permit entry of said normal paraffins and said mono-methyl-branched paraffins but restrictive to prohibit entry of di-branched paraffins, separating, in said second feed separation zone, at separation conditions, by means of said second shape-selective separatory sieve, said di-branched paraffins from said mono-methyl- branched paraffins, recovering from said second feed separation zone a second feed separation zone effluent stream comprising said di-branched paraffins, recovering from said first feed separation zone a first isomerization zone feed stream comprising said normal paraffins and recovering from said second feed separation zone a second isomerization zone feed stream comprising said mono-methyl paraffins, and passing at least a portion of said first, said second or both said first and second isomerization zone feed streams to an isomerization zone maintained at isomerization conditions and containing a isomerization catalyst to produce an isomerization zone effluent stream comprising di-branched paraffins, mono-methyl-branched paraffins and normal paraffins.

Another embodiment of this invention resides in a process for the preparation of a gasoline blending pool comprising an isomerate from a hydrocarbon feed stream mixture containing normal hexane, methyl pentanes and di-methyl butane which comprises passing said feed stream to a multiple molecular sieve feed separation zone containing multiple separatory shape-selective molecular sieves comprising: (1) a molecular sieve of a pore size of 4.5 to 4.5A and (2) a molecular sieve of a pore size intermediate 5.5$\times$5.5 to 4.5$\times$4.5A and excluding 4.5$\times$4.5A, said shape-selective molecular sieves being effective to permit entry of said normal hexane and said mono-methylpentanes and restrictive to prohibit entry of said dimethyl butane and to thereby separate said dimethyl butane from said normal hexane and mono-methylpentanes, recovering said dimethyl butanes as a feed separation zone effluent and recovering said adsorbed normal hexane and mono-methylpentanes and passing said normal hexane and monomethylpentane to an isomerization zone and isomerizing, at isomerization conditions, in the presence of an isomerization catalyst said normal hexane to methyl pentanes and dimethyl butane and isomerizing said mono-methylpentanes to dimethyl butane, and to form an isomerization effluent isomerate stream comprising unisomerized normal hexane, mono-methylpentanes and dimethyl butane.

BRIEF DESCRIPTION OF THE INVENTION

This invention is concerned with the novel use of a multiple select adsorbent molecular sieve system having particular separatory qualities. The sieves are arranged upstream of an isomerization process to treat a feed stream to preserve constituents in the feed stream which would be diminished in value by isomerization. At the same time, this invention provides a means to selectively isomerize n-paraffins and mono-methyl-branched paraffins. The multiple separatory sieve system of this invention comprises a first molecular sieve having a pore size of 4.5×4.5A and being shaped to permit adsorption of normal paraffins in a selective manner vis-a-vis mono-methyl-branched paraffins, di-methyl-branched paraffins, cyclic paraffins and aromatic hydrocarbons and a second molecular sieve having a pore size of 5.5×5.5 to 4.5×4.5A and being selected to permit adsorption of mono-methyl-branched paraffins (and any ancillary normal paraffins) in deference to multi-branched paraffins, cyclic paraffins and aromatic hydrocarbons which can be passed directly to a refinery gasoline blending pool.

DETAILED DESCRIPTION OF THE INVENTION

The schematic process flow of this invention exemplified by FIGS. 2 through 7 of the drawings is initiated by the novel separatory treatment of a hydrocarbon feed material prior to isomerization in a multiple number of at least two discrete separatory sieves. Contemplated feed streams to this isomerization process are comprised mainly of isomeric forms of saturated hydrocarbons having $C_6$ or greater carbon atoms. In order to take full advantage of the highlights of this invention, the feed material should contain an amount of di-branched paraffinic hydrocarbons which ar known for their high octane value worthy of separation. The feed stream can comprise normal paraffins, mono-methyl paraffins and dimethyl paraffins. The carbon numbers of these paraffins are preferably $C_6$ or higher for the normal paraffins mono-methyl-branched paraffins and di-branched paraffins. These feedstocks are usually derived from refinery operations and can contain quantities of $C_5^-$, $C_7^+$, and cyclic paraffins. Olefinic and aromatic hydrocarbons may also be present. When naphthenes and aromatics are present, they will not be significantly adsorbed by the sieve upstream of isomerization and will pass with the dimethyl paraffins directly to the refinery gasoline blending pool without isomerization. This is very advantageous due to the relatively high octane quality of some of the aromatic and naphthenic material derived from this separation.

The preferred feedstocks will contain more than 25 mole percent normal hexane. By use of the process of this invention, the actual hydrocarbon feed stream to the isomerization zone will contain both normal paraffins and mono-methyl paraffins in contrast to other prior art techniques using only a calcium 5A sieve to treat a feed stream and thereby pass only normal paraffins to isomerization.

The multiple molecular sieve pretreatment step which produces the feed stream ultimately passed to the isomerization zone comprises at least two molecular sieves. These can be arranged in separate vessels, or they can be arranged in a stacked flow scheme within one vessel It is important to this invention that the molecular sieves be arranged in a particular order.

The first molecular sieve should have a pore size of 4.5×4.5A or smaller to permit adsorption of normal paraffins and to permit mono-methyl-paraffins, di-branched paraffins, cyclic paraffins and aromatic hydrocarbons to pass through the sieve without adsorption. This first sieve can be exemplified by a calcium 5-A sieve or any other sieve of similar pore dimensions. It is not necessary to size the first sieve to adsorb all of the normal paraffins, but it is preferred so that the second molecular sieve does not have to function as a normal paraffin adsorption sieve The second sieve in this process sequence is exemplified by a molecular sieve which has eight and ten member rings and pore dimensions intermediate 5.5×5.5 and 4.5×4.5A, but excluding 4.5×4.5A (for example, calcium 5-A sieve).

The preferred second molecular sieve of this invention is exemplified by a ferrierite aluminosilicate which exhibits a greatly increased adsorption capacity towards methylpentane relative to a calcium-5A molecular sieve. It is preferred that the ferrierite sieve be present in a hydrogen form, but it alternatively can be exchanged with a cation of an alkali metal, or alkaline earth metal or transition metal cation. The molecular sieves of this invention include ferrierite and other analogous shape-selective materials with pore openings intermediate in dimensions to those of the calcium-5A and ZSM-5 molecular sieves. Other examples of crystalline sieves will include aluminophosphates, silicoaluminophosphates, and borosilicates.

Exemplary of the wide range of aluminophosphates available in the prior art are the following articles:

(1) Synthesis and properties of several aluminophosphate molecular sieves Quinhua, Xu; Dong, Jialu; Yan, Aizhen; Jin, Changtai Dep. Chem., Nanjing Univ. Nanjing, Peopl. Rep. China Acta Phys. Chem., 31(1–2), 99–108 66–3 (Surface chemistry and Colloids)

(2) Synthesis of aluminophosphate molecular sieve AlP4–12 Xu, Wen Yang; Guo, Chang Jie; Do. Tao Shanxi, Peopl. Rep. China J. Inclusion Pheno., 4(4), 325–31 66–63 (Surface Chemistry and Colloids)

(3) Synthesis and properties of new aluminophosphate molecular sieves CNU-n (n=1,2,3) Xu, Qinhua; dong, Jialu; Yan, Aizhen; Jin, Changtai Dep. Chem., Nanjing Univ. Nanjing, Peopl. Rep. China Wuji Huaxue, 1, 74–80

(4) Structural features of aluminophosphate materials with aluminum/ phophorus=1 Bennett, J. M.; Dytrych, W. J.; Pluth, J. J.; Richardson, J. W., Jr.;

Smith, J. V. Inorganic Chemicals and Reactions 78-5 Union Carbide Corp. Tarrytown, N.Y. 10591, U.S.A.

(5) Zeolites, (5), 349–60 75-0 (Crystallography and Liquid Crystals) The structure of coprecipitated aluminophosphate catalyst supports Cheung, T.T.P.; Willcox, K. W.; McDaniel, M. P.; Richardson, Johnson, M. M.; Bronnimann, C.; Frye, J. Phillips, Res. Cebt, Bartlesville, O.K. 74004, U.S.A. J. Catal., 102(1), 10–20 67-1 (Catalysis, Reaction Kinetics, and Inorganic Reaction Mechanisms)

(6) Site energy distribution and catalytic properties of microporous crystalline AlPO4-5 Choudhary, Vasant R.; Akolekar, Deepak B. Chem. Eng. Div., Natl. Chem. Lab. Pune 411 008, India J. Catal., 103(1), 115–25 51-6 (Fossil Fuels, Derivatives, and Related Products)

The silicoaluminophosphate sieves are described in U.S. Pat. Nos. 4,440,871 and 4,654,138, all of the teachings of which are herein incorporated by references. In addition, European Pat. No. 209,997 discloses the use of silicoaluminophosphates for catalytic dewaxing of lube oils. Other technical articles discussing the structure of these select molecular sieves are as follows:

(1) Structure of an aluminosilicophosphate Ito, Masatoki; Shimoyama, Yumiko; Saito, Yoshihiki; Tsurita, Ysaushi; Otake, Masayuki Fac. Sci, Technol., Keio Univ. Yokohama 223, Japan Acta Crystallogr., Sect. C: Cryst. Struct. Commun., C41(12), 1698–700 75-8 (Crystallography and Liquid Crystals)

(2) Adsorption properties of microporous aluminophosphate (AlPO4-5) Stach, H.; Thamm, H.; Fiedler, K.; Grauert, B.; Wieker, W.; Jahn, E.; Oehlmann, G. Cent. Inst. Phys. Chem., Acad. Sci. GDR Berlin-Adlershof 1199, Germ. Dem. Rep. Stud. Surf. Sci. Catal., 28 (New Dev. Zeolite Sci. Technol.), 539–6 66-3 (Surface Chemistry and Colloids)

(3) Molecular sieve effects in carboniogenic reactions catalyzed by silioaluminophosphate molecular sieves Pellet, R. J.; Long, G. N.; Rabo, J. A. Union Carbide Corp. Tarrytown, N.Y. 10591, U.S.A. Stud. Surf. Sci. Catal., 28 (New Dev. Zeolite Sci. Technol.), 843–9 45-4 (Industrial Organic Chemicals, Leather, Fats, and Waxes)

(4) Methanol conversion to light olefins over silicoaluminophosphate molecular sieves Kaiser, Steven W. Union Carbide Corp. South Charleston, W.V. 25303, U.S.A. Arabian J. Sci. Eng., 10(4), 361–6 35-2 (Chemistry of Synthetic High Polymers) 23, 45

(5) Synthesis of aluminosilicophosphate molecular sieves and their adsorption-structural properties Pechkovskii, V. V.; Margulets, A. V.; Eschchenko, L. S. BTI USSR Khim. Khim. Tekhnol. (Minsk), 20, 46–50 78-4 (Inorganic Chemicals and reactions)

(6) Thermal stability and acid resistance of aluminosilicophosphate zeolites Margulets, A. V.; Eshchenoko, L. S.; Greben'ko, N. V.; Pechkovskii; V. V. Beloruss. Tekhnol. Inst. Minsk, USSR Izv. Akad. Nauk SSSR, Neorg. Mater., 22(11), 1878–82 66–3 (Surface Chemistry and Colloids)

Suitable borosilicates are exemplified by the following articles:

(1) Catalytic and acidic properties of boron pentasil zeolites Coudurier, G.; Vedrine, J. C. Inst. Rech. Catal., CNRS Villeurbanne F 69626, Fr. Stud. Surf. Sci. Catal., 28 (New Dev. Zeolite Sci. Technol.), 643–52 67-1 (Catalysis, Reaction Kinetics, and Inorganic Reaction Mechanisms)

(2) Quantum mechanical calculation on molecular sieves. 1. Properties of the Si-0-T (T si, Al, B)- bridge in zeolites Derouane, E. G.; Fripiat, J. G. Cent. Res. Lab., Mobil Res. and Dev. Corp. Princeton, NJ 08540, USA J. Phys. Chem., 91(1), 145–8

(3) Acidity and catalytic activity for methanol transformation over modified borosilicate and aluminosilicate zeolites Hegde, S. G.; Chandwadkar, A. J. Natl. Chem. Lab. Poona 411 008, India Adv. Catal., [Proc. —Natl. Symp. Catal.], 7th, 163–9. Edited by: Prasada Rao, T.S.R. Wiley: New York 51-11 (Fossil Fuels, Derivatives, and Related Products)

The aluminophosphate, silicoaluminophosphate and borosilicate molecular sieves will have a pore opening intermediate between 5.5×5.5 and 4.5×4.5A but excluding 4.5×4.5A as shown in Table I.

The following Table I demonstrates the correct pore size dimensions of the second molecular sieve versus other sieves which will not perform with the same adsorption characteristics as a ferrierite-sized molecular sieve.

TABLE I

| Molecular Sieve | Pore Opening Dimensions (A) | Size |
|---|---|---|
| chabazite | 3.9 × 4.1 | TOO SMALL |
| zeolite A | 3.9 × 4.1 | TOO SMALL |
| erionite | 3.6 × 5.2 | TOO SMALL |
| Ca-5A | 4.5 × 4.5 | TOO SMALL |
| ferrierite | 4.5 × 5.5 | CORRECT SIZE |
| ZSM-5 | 5.4 × 5.6 | TOO LARGE |
| offretite | 6.0 × 6.0 | TOO LARGE |
| mordenite | 6.7 × 7.0 | TOO LARGE |
| omega | 7.4 × 7.4 | TOO LARGE |
| Y zeolite | 7.4 × 7.4 | TOO LARGE |

It is also feasible that the molecular sieve can comprise a large pore zeolite that has been ion exchanged with cations to diminish the effective pore size of the sieve to within the afore mentioned range of dimensions.

Thus, any molecular sieve having pore dimensions intermediate those of 5.5×5.5 and 4.5×4.5A will be considered as a preliminary candidate of the select molecular sieve of this invention.

The sequence of the sieves, whether in discrete vessels or in a stacked variety, is very important to this invention. If the sieves are interchanged and the second selectively sized sieve is placed prior to the first selectively sized sieve, the process loses its effectiveness because the larger sieve will rapidly fill with normal paraffins, prohibiting the efficient adsorption of monomethyl-branched paraffins.

The respective sieves should always be arranged in a process sequence to first provide adequate adsorption of the normal paraffin hydrocarbons, and then, second adsorption of the mono-methylparaffins. Each of the respective sieves can be provided with a common desorbent stream or each sieve may have its own desorbent stream. The desorbent is preferably a gaseous material such as a hydrogen gas stream, which will not have a deleterious effect upon subsequent downstream isomerization. Any of the hydrocarbons desorbed from these sieves by the desorbent, in addition to the hydrogen, can be passed together or separately to an isomerization zone without harm to the isomerization catalyst. The desorbent stream from the first molecular sieve (hydrogen+n-paraffins) can be passed to a isomerization zone possessing a catalyst selected for the isomerization of normal paraffin hydrocarbons while the desorbent and mono-methylparaffins derived from the second molecular sieve are passed to an isomerization zone possessing a catalyst selected for the isomerization of the mono-methyl-paraffins.

The adsorption/desorption conditions typically utilized with either or both of the molecular sieves of this invention comprise a temperature of from about 75° C. to about 400° C. and a pressure of from about 2 bar to about 42 bar. The adsorption and desorption conditions are very similar to the conditions present in the separation sieve or sieves normally operated downstream of isomerization.

The paraffinic feed material is passed through an individual isomerization reactor or a multiple number of isomerization zones each having an isomerization catalyst therein. The isomerization catalyst is preferably a zeolite with a catalytic metal dispersed thereon. Exemplary of such a catalyst is mordenite with platinum present in a range of 0.005 wt% to 10.0 wt% with a preferred range being from 0.2 to 0.4 wt % Other zeolite molecular sieves are also viable which have a silica to alumina molar ratio of greater than 3 and less than 60 and preferably less than 15. The zeolite molecular sieves may have many polyvalent metal cations exchanged with the sieve, such as those of the alkali metals or alkaline earth metals. The catalytic metals associated with the isomerization function are preferably noble metals from Group VIII of the Periodic Table of elements. These can be exemplified by such metals as platinum, palladium, osmium, ruthenium, etc. The isomerization catalyst can be present per se or it may be mixed with a binder material. Other equivalent isomerization catalysts can be utilized within the confines of this invention; however, the mordenite-Group VIII metal catalyst is preferred. For example, a faujasite molecular sieve may be utilized but has poorer selectivity than mordenite.

The isomerization conditions present in the isomerization zone ar those selected to maximize the conversion of normal paraffins and mono-methyl-paraffins to di-methyl-branched paraffins. This type of isomerization is favored in the vapor phase with a fixed bed of isomerization catalyst. Typical operating temperatures include from 200° to 400° C. with pressures of about 10 to 40 bar. The isomerization process, which is limited in octane upgrading by thermodynamic equilibria, is frequently measured at 10 points. Even at these select conditions, the effluent from the isomerization reactor will still contain substantial (e.g. 20 to 30 wt %) normal paraffins and mono-methyl-branched paraffins which are unreacted or partially reacted due to the aforementioned equilibrium.

One of the advantageous aspects of this invention is the fact that di-methyl-branched paraffins, cyclic paraffins and aromatics are not passed to the isomerization zone. The isomerization reaction has a chemical equilibrium. The exclusion of the dimethyl paraffins from the isomerization zone is advantageous for maximizing the quantity of di-methyl paraffins produced during isomerization while at the same time, reducing the number of normal paraffins which remain unisomerized in the isomerization zone effluent stream. After isomerization, the isomerization zone feed stream will contain unisomerized normal paraffins, mono-methyl paraffins and di-branched paraffins.

The isomerization zone effluent stream, after suitable removal of light ends which are sometimes generated during isomerization, can be sent directly to the gasoline pool or it can be passed to a separation zone which will preferably comprise from three to eight adsorbent beds which can be modified to operate in an adsorption/desorption mode as exemplified in U.S. Pat. No. 4,210,771, all of the teachings of which, in regard to the function of adsorption/desorption are herein incorporated by reference. This separation zone after isomerization will contain a multiple number of one or more types of separatory sieve which can be exemplified by such sieves as a calcium-5A sieve or a ferrierite sieve. The calcium-5A sieve is capable of adsorbing virtually no methylpentane (no dimethylbutane) and thus will recycle only normal paraffins to complete isomerization.

In contrast to use of a singular molecular sieve, a multiple, sequential molecular sieve such as used in the instant separatory sieve upstream of isomerization can be utilized to form a recycle stream of mono-methyl-branched paraffins and normal paraffins. The aforementioned examples of particular molecular sieves are exemplary of molecular sieves which ca be utilized to separate the isomerization zone effluent stream to form the advantageous mono-methyl-branched paraffin and normal paraffin recycle stream. It is not necessary that all of the normal paraffins (in the case of a calcium-5A sieve) or all of the mono-methyl-branched paraffins and normal paraffins (in the case of a ferrierite-sized molecular sieve) be recycled to isomerization. However, for economic purposes it is sometimes beneficial that all paraffins containing branching with a single methyl moiety be recycled until an equilibrium is reached maximizing the quantity of di-methyl branched paraffins.

In this later process, two gasoline blending component streams are acquired. First the material which will elute through the preliminary sieve upstream of isomerization will contain very high octane paraffins in addition to an aromatics and naphthenes present in the feed. The second gasoline blending component will be derived downstream of the separatory sieve which acts on the isomerization zone effluent. These two gasoline blending streams can be combined and utilized as a single blending component or they can be used individually.

Alternatively, a preferred embodiment of this process takes place where the effluent from the isomerization reactor is recycled back and mixed with the unsegregated feed stream. This permits the isomerate to be segregated simultaneously and i commingled association with the feed. This minimizes capital cost and reduces the complexity of operation by performing two segregations in a single set of vessels.

BRIEF DESCRIPTION OF THE DRAWINGS

FIG. 6 shows a schematic flow of the novel process of this invention utilizing multiple molecular sieves upstream of isomerization wherein the material removed from the molecular sieves is passed to separate selective isomerization zones which produce an isomerate which is separated by multiple molecular sieves downstream of isomerization.

FIG. 7 shows a flow scheme of the novel process of this invention which, like FIG. 6, utilizes separate isomerization zones for each desorbate from the select, sequential molecular sieves located on the feed stream.

DETAILED DESCRIPTION OF THE DRAWINGS

Figure 1:
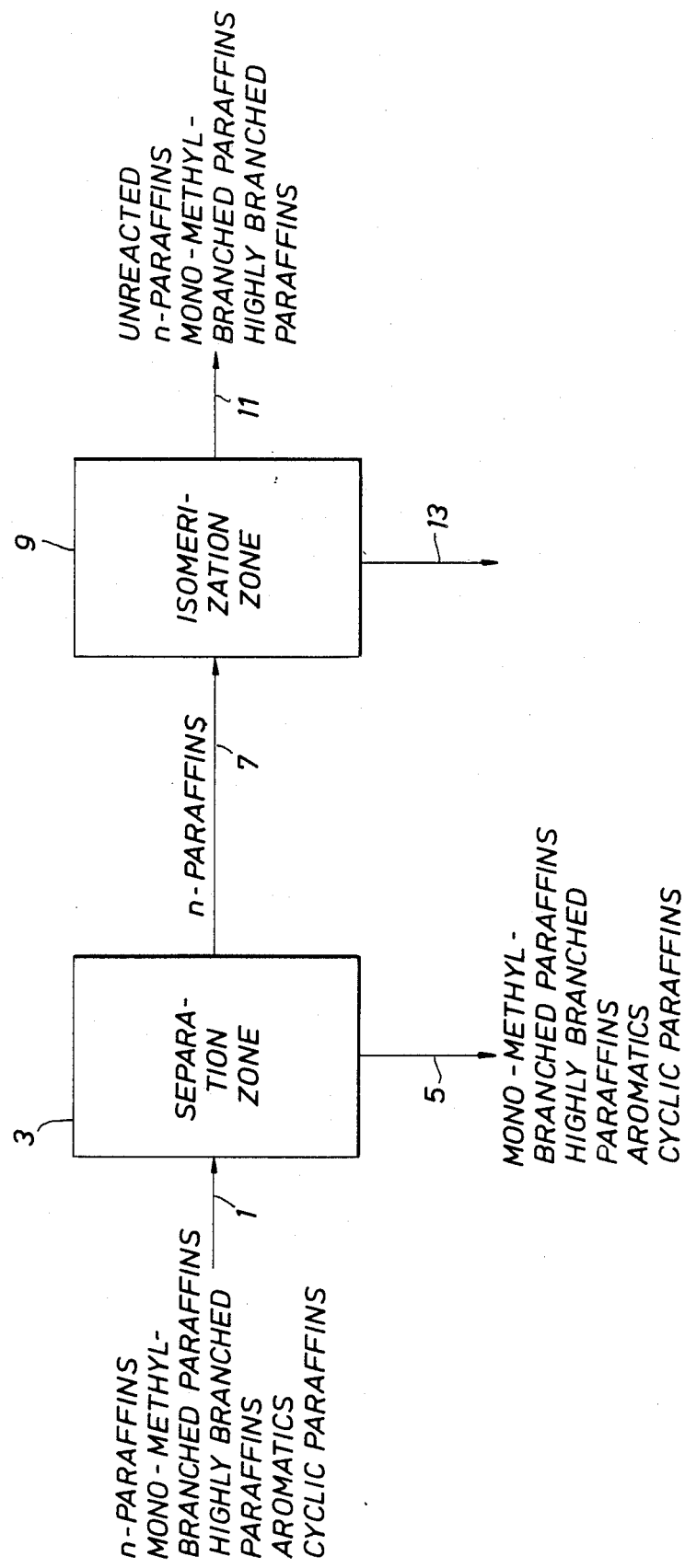
FIG. 1 shows a schematic flow of the process of the prior art.

In FIG. 1 a feedstream comprising a fresh feed having, for example, 4 mol % $C_1$ to $C_5$; and 93 mol % $C_6$ paraffins with small quantities of cycloparaffins, aromatics, and $C_7+$ paraffins are passed through conduit 1 into a separatory zone 3 having at least three and preferably up to 8 adsorbent beds of a molecular sieve such as a calcium-5A zeolite sieve to separate feed constituents. The calcium-5A sieve will entrap or adsorb normal paraffins while allowing mono-methyl-branched paraffins and other branched paraffins to pass through the separation zone and be recovered in conduit 5 as a gasoline blending component. After applicable desorption with means not shown, a normal paraffin stream in conduit 7 is withdrawn from the separatory zone 3 and passed to isomerization zone 9. This zone is maintained at conditions selected to maximize the degree of branching of the product stream 11. A typical isomerization catalyst as described at Column 5 of U.S. Pat. No. 4,210,771 can be present in this prior art process. If desirable, a vented hydrogen or light hydrocarbon gas stream can be removed from the isomerization zone in conduit 13. An effluent stream from isomerization zone 9 is removed in conduit 11 containing normal paraffins, mono-methyl-branched paraffins and more highly branched paraffins (e.g. ethylpentane, dimethylbutane etc.).

Figure 2:
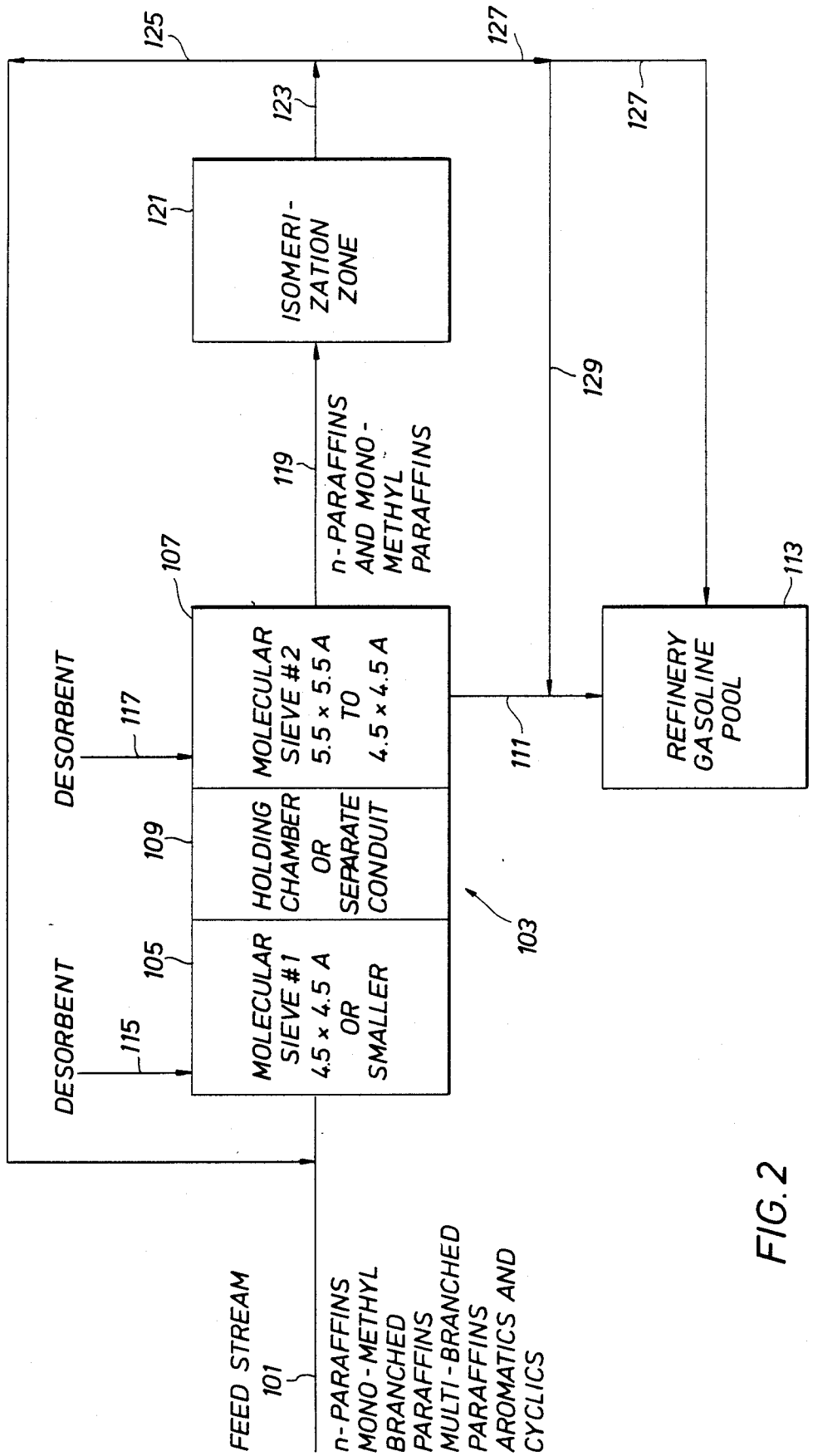
FIG. 2 shows a schematic flow of the novel process of this invention utilizing a multiple number of molecular sieves upstream of isomerization but no molecular sieves downstream of isomerization.

FIG. 2 demonstrates the use of the instant invention on a similar type of hydrocarbon feed stream as exemplified in FIG. 1 with the advantage of the use of a multiple number of select molecular sieves upstream of isomerization. The feed stream in conduit 101 is passed to sieve separation zone 103 which may comprise either a stacked configuration or can comprise a series flow of vessels in a unitary configuration. Adsorption zone 103 contains at least two molecular sieves 105 and 107. These sieves may be separated by a holding chamber or separate conduit 109.

Molecular sieve #1 (105) is a zeolite having pore size of from 4.5 to 4.5A or smaller. A calcium-5A zeolite is a particular type of preferred molecular sieve. Molecular sieve 107, referred to as molecular sieve #2, has a pore size of 5.5×5.5 to 4.5×4.5A but excludes 4.5×4.5A. This molecular sieve will preferably comprise a ferrierite and may be produced by any known ferrierite synthesis method as exemplified in U.S. Pat. Nos. 4,016,245 and 4,251,499. See also J. A. Martens "Selectivity Induced by the Void Structure of Zeolite Beta and Ferrierite in Hydroconversion Hydrocarbon of n-Decene," pages 115. 119.

The first molecular sieve 105 selectively adsorbs normal paraffins in preference to mono-methyl-branched paraffins, multi-branched paraffins, cyclic paraffins and aromatic hydrocarbons. After the normal paraffins have been substantially removed from the fee stream, contact is made with molecular sieve #2 (107). In this particular sieve, mono-methyl-branched paraffins are adsorbed while multi-branched paraffins, cyclic paraffins and aromatic hydrocarbons are passed through the sieve without adsorption. The multi-branched paraffins, cyclic paraffins and aromatics have a high octane rating and are thus removed from pretreatment sieve system 103 via conduit 111 and passed directly to refinery gasoline pool 113 for further blending with gasoline-based components. The normal paraffins can be desorbed from sieve 105 by means of a desorbent, preferably hydrogen, added to sieve 105 through conduit 115. If desired, a separate desorbent can be added to sieve 107 through conduit 117 or in the alternative, if a unitary vessel is utilized in a stacked-bed configuration, the desorbent may simply be added at one end of separatory sieve system 103.

The material removed from zone 107 in conduit 119 comprises the isomerization zone feed stock. This feed material will be a mixture of normal paraffins and mono-methyl-branched paraffins which are added to isomerization zone 121.

In isomerization zone 121, a molecular sieve isomerization catalyst is located to selectively convert normal paraffins to mono-methyl paraffins and di-branched paraffins and to convert mono-methyl paraffins to di-branched paraffins. The chemical equilibrium in the isomerization zone results in a mixture removed from isomerization zone 121 in conduit 123 having di-branched paraffins, normal paraffins and mono-methyl paraffins. Without further separation, this stream can be divided into a recycle stream 125 and passed back to feed stream 101 or passed to product stream 127, which can be added directly to gasoline blending pool 113 o diverted through line 129 and added to conduit 111. Of course, it is within the scope of this invention that the hydrocarbon content in conduit 127 (the isomerate) can be utilized separate and distinct from that high octane material added to refinery gasoline pool 113 via conduit 111. The recycle stream in conduit 125 can be added to feed stream 101 or to either separatory sieve 105 or 107. It is also possible to add recycle stream 125 directly to isomerization zone 121.

Figure 3:
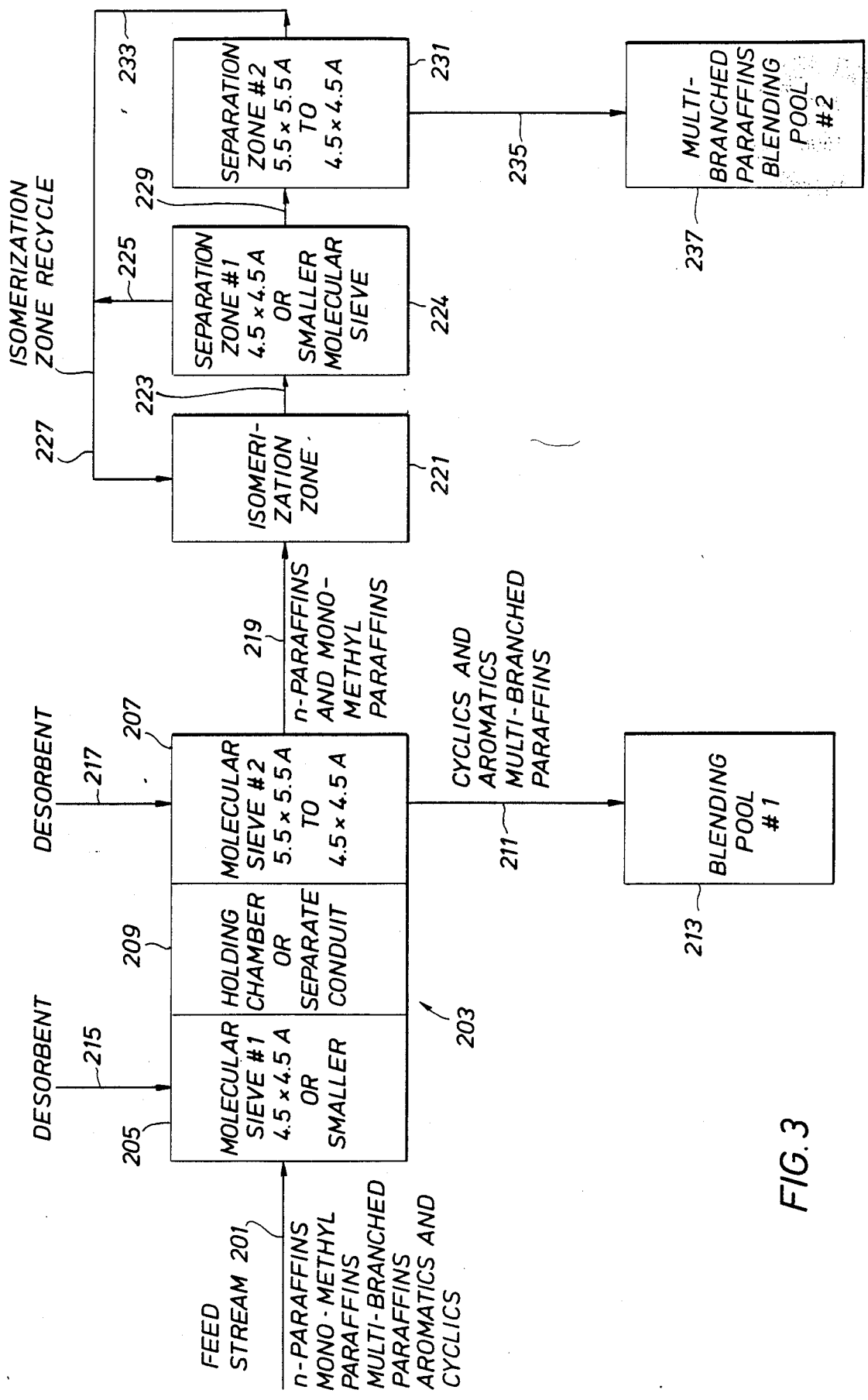
FIG. 3 shows a schematic flow of the novel process of this invention utilizing multiple molecular sieves upstream of isomerization and multiple molecular sieves downstream of isomerization.

FIG. 3 demonstrates the use of this process on a similar type of hydrocarbon feed material as exemplified in FIG. 1 with the advantage of the multiple pretreatment sieves and multiple separatory sieves downstream of isomerization. A feed stream similar to that described previously is added in conduit 201 to separatory sieve system 203. Again, this may comprise either a series of separatory sieves individually located or, in the alternative, a stacked bed of sieves containing both of the applicable molecular sieves. For sake of convenience, the drawings show the multiple number of sieves as molecular sieve #1 (205) and molecular sieve #2 (207). An intermediate zone 209 is also present, but is not necessary to the functioning of this particular process.

Molecular sieve #1 (205) comprises a sieve having a pore dimension of 4.5 x 4.5A or smaller. Exemplary of this sieve is a calcium-5A sieve. This sieve is selected for its ability to adsorb normal paraffins.

Sieve 207 is exemplified as molecular sieve #2 and has a pore dimension of from about 5.5×5.5 to 4.5×4.5A, excluding 4.5A. A ferrierite type of molecular sieve exemplifies this type of sieve which is selective for the adsorption of normal paraffins, if any remain from sieve 205, and for mono-methyl paraffins.

Di-branched paraffins or multi-branched paraffins, in addition to cyclic paraffins and aromatics are removed in conduit 211 and passed to gasoline blending pool 213 for blending with a gasoline-based material. The normal paraffins adsorbed in sieve 205 and the mono-methyl paraffins adsorbed in conduit 207 are desorbed through the use of a desorbent such as hydrogen added through conduits 215 and/or 217 to separation system 203. Hydrocarbon material is withdrawn in conduit 219 and passed to isomerization zone 221. The hydrocarbon material in conduit 219 comprises normal paraffins and mono-methyl paraffins. Isomerization zone 221 contains an isomerization catalyst and is maintained at isomerization conditions to convert the normal paraffins to mono-methyl paraffins and the mono-methyl paraffins to di-methyl paraffins. The effluent from isomerization zone 221 is withdrawn in conduit 223 and contains multi-branched paraffins in addition to normal paraffins and mono-methyl paraffins. It is advantageous to separate the normal paraffin for recycle to ultimate isomerization. For this reason, a first separation zone 224 is provided having a molecular sieve of pore dimensions of 4.5×4.5A or smaller. This separation produces a normal paraffin recycle stream withdrawn from separator 224 through conduit 225, which is recycled to isomerization through conduit 227. The effluent (non-adsorbed hydrocarbons) from separation zone 224 is withdrawn in conduit 229 and usually comprises di-methyl paraffins and mono-methyl paraffins. It is advantageous to recycle mono-methyl paraffins to isomerization zone 221. For this reason, stream 229 is added to separation zone 231 for separation of the di-methyl paraffins from the mono-methyl paraffins. Separation zone 231 contains a molecular sieve having pore dimension of 5.5×5.5 to 4.5×4.5A. A recycle stream is removed from separator 231 in conduit 233. The contents of this stream will be predominantly mono-methyl-paraffins which are added to recycle stream 225 to form recycle stream 227.

A stream comprising multi-branched paraffins (isomerate) is withdrawn from second separation zone 231 in conduit 235 and passed to a second blending pool 237 for use in blending with a gasoline range boiling material. It is within the scope of this invention that blending pool 213 and blending pool 237 comprise the same zone or they may be operated independent one another.

Figure 4:
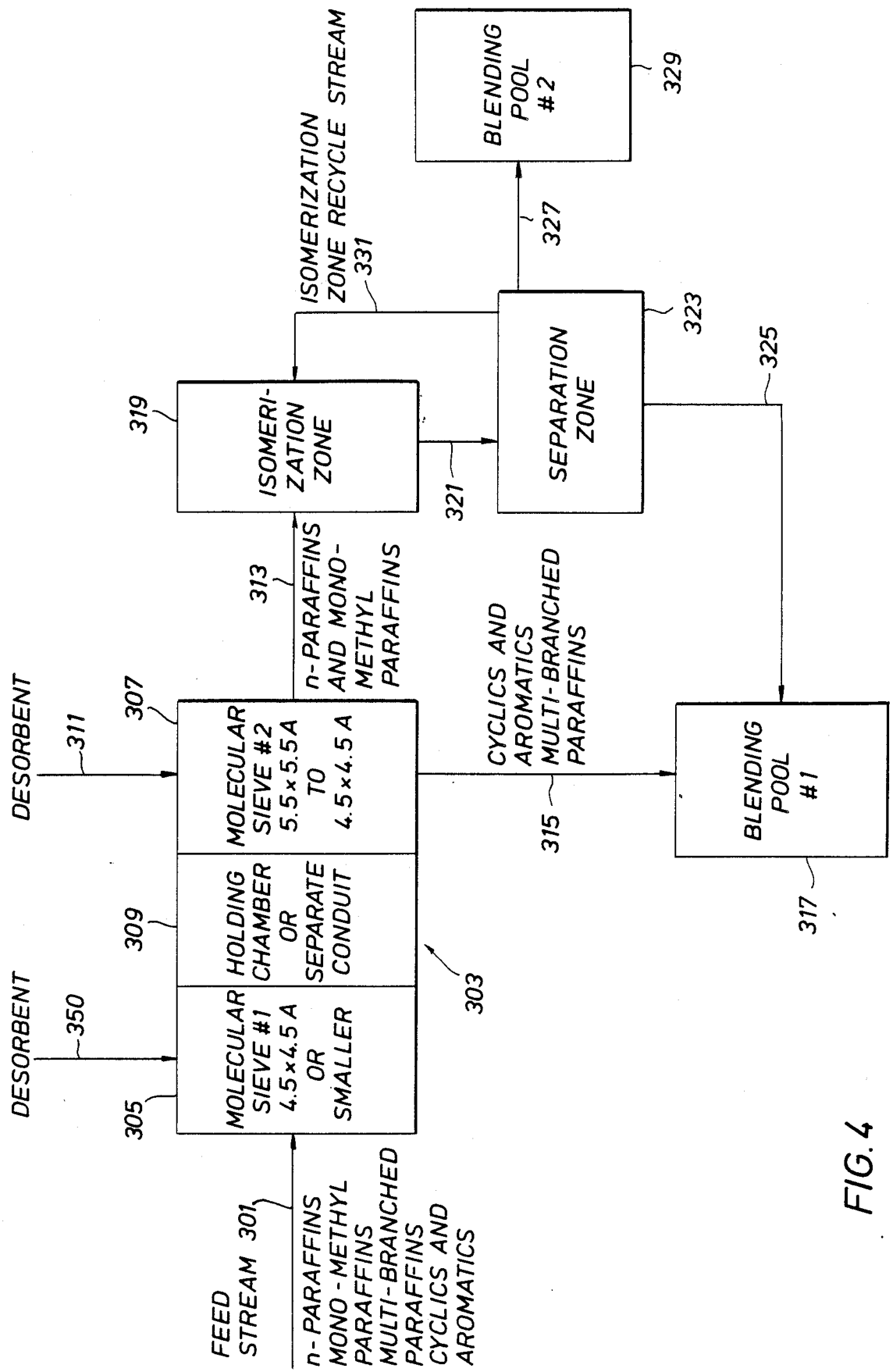
FIG. 4 shows a schematic flow of the novel process of this invention utilizing multiple molecular sieves upstream of isomerization and a unitary molecular sieve downstream of isomerization.

FIG. 4 demonstrates the use of this process on a similar type of hydrocarbon feed stream as exemplified in FIG. 2 with the advantage that the isomerization zone effluent is passed to a separation zone for the removal of select high octane material and the recycle to the isomerization zone of material which lacks the octane value desired. A feed stream in conduit 301 is added to pretreatment separation zone 303 which comprises at least two different molecular sieves. These sieves may be in a stacked bed configuration or in a series flow configuration in one or more vessels. Molecular sieve #1 (305) comprises a molecular sieve having a pore dimension of between 4.5×4.5A or smaller. Calcium-5A is an example of one such sieve. Molecular sieve #2 (307) has a pore diameter of between 5.5×5.5 to 4.5×4.5A excluding 4.5×4.5A and is exemplified by ferrierite. An intermediate void space is shown as 309, which is optional and not necessary to have an operable process. It is also contemplated that these sieves comprise a multiple number of alternating sieves, such that when on sieve is being desorbed another is being used as an adsorbent. A desorbent material is added to sieve 305 through conduit normal paraffins and mono-methyl paraffins and form separation zone effluent 313. A blending stream comprising cyclic paraffins aromatic paraffins and multi-branched paraffin is removed from zone 307 in conduit 315 and passed to blending pool 317 for use in the manufacture of gasoline. Effluent stream 313 comprises a feed material for isomerization zone 319. This zone contains an isomerization catalyst and is maintained at isomerization conditions to produce a maximum quantity of di-branched paraffins from the normal paraffins and mono-methyl paraffins. The effluent from isomerization zone 319 is removed in conduit 321 and contains normal paraffins, mono-methyl paraffins and di-branched paraffins. These materials are added to separation zone 323, which can contain either a calcium-5A sieve, a ferrierite-type sieve or a combination of both. Depending on the type of sieve present in separation zone 323, a blending component (isomerate) is removed in conduit 325 and passed to blending pool 317. If desired, this blending material can be removed from separation zone 323 in conduit 327 and added to a second blending pool 329. Where the separatory sieve is a calcium-5A sieve, isomerization zone recycle stream 331 will be comprised of normal paraffins, while streams 325 and 327 will be comprised of mono-methyl paraffins. In an embodiment where separation zone 323 is a ferrierite-type molecular sieve, isomerization zone recycle stream 331 will be comprised of normal paraffins and mono-methyl paraffins while blending streams 325 and 327 will be comprised of mainly di-branched paraffins.

Figure 5:
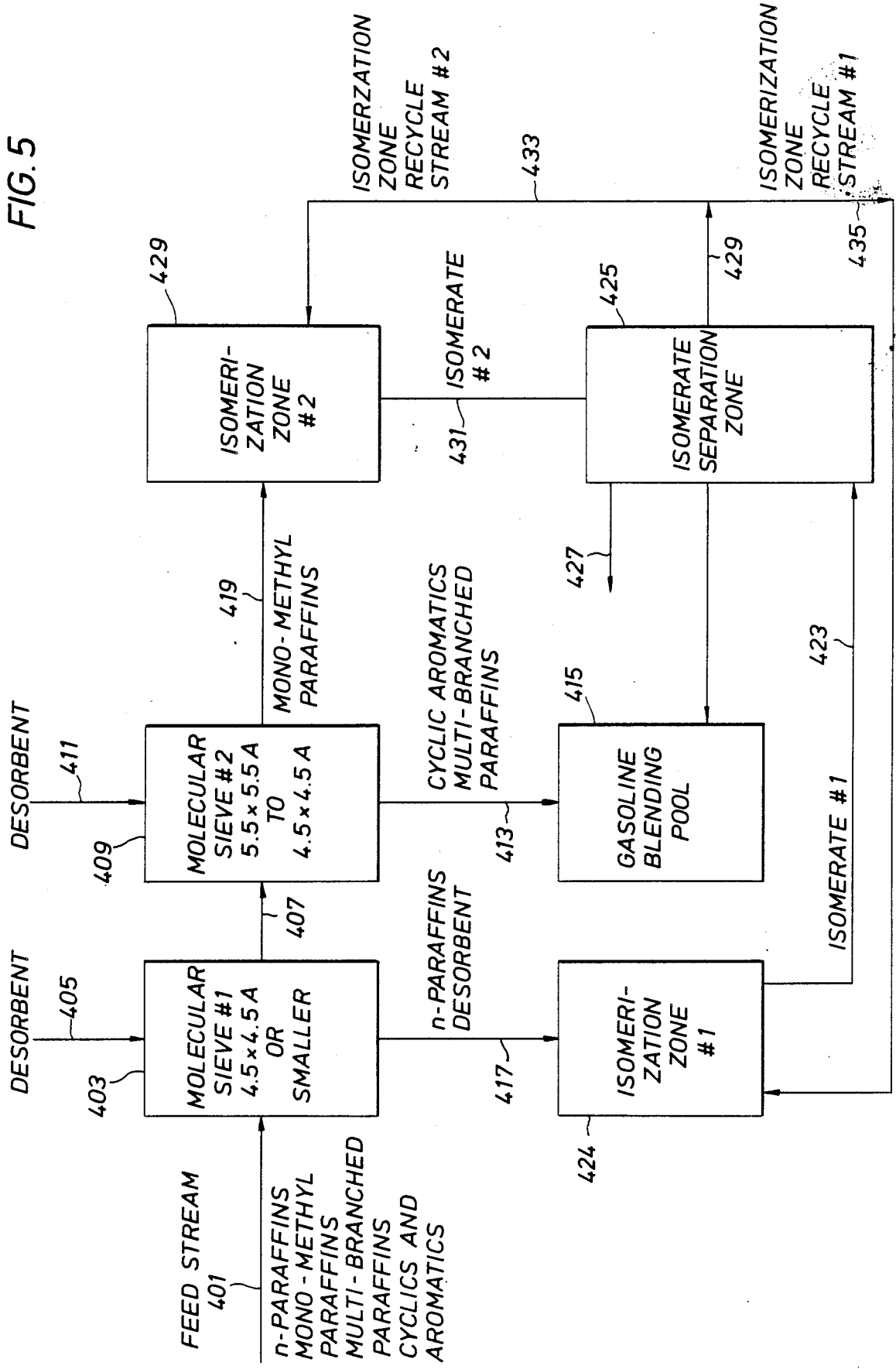
FIG. 5 shows a schematic flow of the novel process of this invention utilizing a multiple number of molecular sieves up stream of isomerization wherein the material separated from the multiple molecular sieves is passed to selective isomerization zones.

FIG. 5 demonstrates the use of this process on a similar type of hydrocarbon feed stream as exemplified in FIG. 1 with the advantage that the select separation of the feed stream will provide feed to different selective isomerization reactors. Feed stream 401 passes a feed stream containing normal paraffins, mono-methyl paraffins, multi-branched paraffins, cyclic paraffins and aromatic hydrocarbons to molecular sieve #1 (shown as 403). This molecular sieve will preferably be in a discrete vessel in order to selectively adsorb normal paraffins from the feed material. A desorbent such as hydrogen may be added through conduit 405 to remove the adsorbed normal paraffins after the flow of the feed material i conduit 401 is stopped. The unadsorbed effluent from sieve #1 (403) is removed in conduit 407 comprising mono-methyl paraffins, multi-branched paraffins, cyclic paraffins and aromatic hydrocarbons and passed to molecular sieve #2 (409) having a pore size of 5.5×5.5 to 4.5×4.5A and excluding 4.5×4.5A. This is exemplified by ferrierite. A desorbent such as hydrogen may be added in conduit 411 to remove the mono-methyl paraffins adsorbed by sieve 409.

A high octane product of this invention is removed in conduit 413 which contains multi-branched paraffins, cyclic paraffins and aromatic hydrocarbons. This material is added to gasoline blending pool 415. Each sieve, 403 and 409, is responsible for providing an effluent respectively shown as 417 and 419. Effluent stream 417 contains desorbent and normal paraffins. These ar added to first isomerization zone 421 which contains an isomerization catalyst selective for the conversion of the normal paraffins to mono-methyl paraffins and multi-branched paraffins. The conditions maintained in isomerization zone 421 are those conditions which are most conducive to the preparation of the multi-branched paraffins. An isomerate is removed in conduit 423 from isomerization zone 421 and passed to isomerate separation zone 425 for separation of the high-octane valued materials from the low-octane valued materials. The multi-branched or, if desired, mono-methyl branched paraffins can be removed as gasoline blending agents in conduit 427 and used as appropriate or the same may be blended into gasoline pool 415. Depending on the separation qualities of the sieve in the isomerate separation zone, a separation effluent is provided in withdrawal conduit 429.

The effluent from molecular sieve 409 in conduit 419 comprises mainly mono-methyl paraffins which is passed to isomerization zone 429 maintained at conditions selected to cause maximum conversion of mono-methyl paraffins to multi-branched paraffins. An isomerization catalyst is present in isomerization zone 429 which is chosen to maximize the production of multi-branched paraffins from mono-methyl paraffins. The effluent from isomerization zone 429 is removed as a second isomerate stream 431 and passed to isomerate separation zone 425. Isomerate stream 431 will comprise mono-methyl paraffins and di-branched paraffins. Separation will be effected on the components of stream 431 as well as those of similar components in stream 423 and withdrawn in withdrawal conduit 429. This may be divided into recycle stream 433 (passed to isomerization zone 429) or conduit 435 (passed to isomerization zone 421). Either of these two recycle streams may be mixed or added at other places in the process.

FIG. 6 demonstrates the use of this process on a similar type of hydrocarbon feed stream as exemplified in FIG. 1 with the advantageous use of multiple isomerization reactors connected to multiple separatory sieves. A feed stream 501 passes a feed comprising normal paraffins, mono-methyl paraffins, multi-branched paraffins, cyclic paraffins and aromatic hydrocarbons to molecular sieve unit 503 which contains molecular sieve #1 (505). This molecular sieve has a pore dimension of 4.5 to 4.5A or smaller and can be exemplified by a calcium-5A sieve. This sieve adsorbs normal paraffins. The unadsorbed effluent from the first molecular sieve 505 is withdrawn from zone 503 in conduit 509 and contains mono-methyl paraffins, multi-branched paraffins, cyclic paraffins and aromatic hydrocarbons. This material is utilized as a feed for the second molecular sieve contained in separatory unit 511, shown as sieve 513. This sieve has a pore dimension of about 5.5×5.5 to 4.5×4.5A and excludes 4.5×4.5A. This high octane stream may be removed as a blending material in conduit 515 and passed to blending pool 517. Where desired a desorbent stream 519 may be provided to remove mono-methyl paraffins from sieve 513 which leaves separation unit 511 in conduit 521. Desorbent 507 added to sieve 505 will result in the removal of desorbent and normal paraffin from unit 503 in conduit 523. This material is added to isomerization zone 525 wherein an isomerization catalyst is maintained at isomerization conditions effective to result in the maximum production of multi-branched paraffins from the normal paraffins of the feed material in conduit 523. The isomerization zone effluent is removed in conduit 527 and will comprise normal paraffins, mono-methyl paraffins and multi-branched paraffins. The hydrocarbon components in stream 527 are passed to a first separation zone 529 (referred to as separation zone #1A). This zone preferably comprises a molecular sieve 531 which is very similar in nature to molecular sieve 505. For this reason, normal paraffins are removed after desorption in conduit 533 and passed back to isomerization unit 525 by means of recycle conduit 535. Mono-methyl branched paraffins and multi-branched paraffins pass unadsorbed through separation zone 529 via conduit 537 and pass to a second separation zone 539, (shown as separation zone #1B). A molecular sieve 541 is present in second separation zone 539 which is very similar to molecular sieve 513. An unadsorbed gasoline blending material (isomerate) comprising multi-branched paraffins is removed in conduit 543 and passed to gasoline blending pool 517 or utilized individually. A recycle stream in conduit 545 is withdrawn from separation zone 539 is passed individually to isomerization zone 525, or alternatively a recycle stream is withdrawn in conduit 547 which is combined with conduit 533 to make up isomerization zone recycle stream 535.

The desorbed effluent from molecular sieve 513 in conduit 521 comprises predominantly mono-methyl paraffins. These are added to isomerization zone 547 which contains an isomerization catalyst selected for its high conversion of mono-methyl paraffins and maintained at isomerization conditions suitable to maximize the production of multi-branched paraffins from the mono-methyl paraffins. An effluent stream in conduit 549 is withdrawn from isomerization zone 547 which comprises normal paraffins, mono-methyl paraffins and di-branched paraffins. This stream is added to separation zone 551, (shown as separation zone #2A). The molecular sieve contained in separation zone 553 is very similar to sieve 505. For that reason, a normal paraffin recycle stream can be desorbed therefrom and removed in conduit 555 and passed in conduit 567 to isomerization zone 547. The hydrocarbon stream minus the normal paraffins is removed from separation zone 553 via conduit 559 and passed to second separation zone 561, (shown as separation zone #2B). The molecular sieve contained therein, 563, is very similar to the molecular sieve 513. For this reason, a mono-methyl paraffins recycle stream is developed in conduit 565 and passed directly to isomerization reactor 547. If necessary, a separate desorbent stream can be removed in conduit 567 and combined with the normal paraffins from conduit 555 to make up recycle stream 567. A third blending component is obtained from separation sieve 563 containing mainly multi-branched paraffins in conduit 569 which is added to gasoline pool 517 or utilized as the refiner deems necessary in the blending of gasoline with the base materials.

Yet another process option is to redirect stream 545 of FIG. 6 which comprises mono-methyl branched hydrocarbons to isomerization zone #2 (547) which contains a catalyst selected for its high conversion of mono-methyl branched hydrocarbons to multiple branched hydrocarbons and operated at conditions to optimize isomerization of mono-methyl branched hydrocarbons. Yet a further process option is to redirect stream 555 of FIG. 6 which comprises normal paraffins to isomeration zone #1 (525) which contains a catalyst selected for its high conversion of normal paraffins and operated at conditions to optimize isomerization of normal paraffins.

The process shown in FIG. 6 can be greatly simplified and reduced in capital cost as shown in FIG. 7. Unlike FIG. 6 however, the effluents of both isomerization zones are recycled to the unsegregated feed. In this way the molecular sieves o the feed perform both the feed segregation and the product segregation with great savings in capital costs and operational flexibility while enjoying the advantage of isomerization zones which are specifically optimized for the particular select desorbate. FIG. 7 shows a process in which the sequentially arranged molecular sieves 605 and 613 segregate the feed components as well as the isomerates.

A feed stream is treated in respective molecular sieves 605 and 613 as shown in sieves 505 and 513 of FIG. 6. Effluent from sieve 605 is passed to the first isomerization zone in conduit 623. This stream is composed mainly of n-paraffins which are isomerized to mono-methyl paraffins and di-methyl paraffins. Effluent in stream 609 contains the hydrocarbon content of feed 601 minus the n-paraffins adsorbed in sieve 605. Passage to the second molecular sieve 613, having a pore size of 5.5×5.5 to 4.5×4.5A excluding 4.5×4.5A, results in adsorption of an n-paraffins remaining unadsorbed in sieve 605 and mono-methyl paraffins. Di-methyl paraffins, aromatics and cycloparaffins which are not adsorbed in either sieve 605 or 613 are passed to blending pool 617 via conduit 615.

Two different isomerization catalysts are provided in isomerization zones 625 and 647. The catalyst in zone 625 can be selected to maximize the isomerization of n-paraffins in conduit 623. The catalyst in zone 647 can be selected to maximize isomerization of the mono-methyl pentanes in stream 621. Both of these respective zones produce effluents, respectively zone 625 effluent 627 and zone 647 effluent 649. These effluent streams can be passed in whole or in part back to pre-isomerization separation via conduit 661.

ILLUSTRATIVE EMBODIMENTS

The instant examples are given as examples of the instant process and the benefit achieved by situating the select molecular sieve before isomerization of the hydrocarbonaceous material.

EXAMPLE 1

In this example, sorption capacities of sodium ferrierite, calcium-5A and sodium ZSM-5 sieves were determined in regard to normal hexane, 3-methylpentane and 2,3-dimethylbutane. The particular denoted zeolite was placed on a pan in a Cahn balance, the sample chamber was evacuated, and heated to 550° C. for one hour. The particular zeolite was thus dried and following drying was cooled to 105° C. At this time, hydrocarbon vapors were admitted to the evacuated chamber to a level of 100 torr. Weight changes due to the adsorption of hydrocarbon into the zeolite were recorded. An exposure time of three hours was allowed for the branched hydrocarbons to approach equilibrium weight, whereas an exposure time of only one half hour was required for normal hexane. The results of this adsorption are shown in Table 2. Each combination of zeolite plus solvent was subjected to at least three separate determinations. Listed in the Table are results of individual determinations, as well as means and standard deviation values for each set of determinations.

TABLE 2

| Hydrocarbon | Weight of HC Adsorbed (mg/g) | | |
|---|---|---|---|
| | Ca-5A | Na-Ferrierite | Na-ZSM-5 |
| 2,3-Dimethylbutane | 1.6 | 2.1 | 59.4 |
| | 1.3 | 1.7 | 59.7 |
| | 1.9 | 1.9 | 61.1 |

TABLE 2-continued

| Hydrocarbon | Weight of HC Adsorbed (mg/g) | | |
|---|---|---|---|
| | Ca-5A | Na-Ferrierite | Na-ZSM-5 |
| | 2.4 | 1.8 | — |
| MEAN + STD DEV: | 1.8 ± 0.4 | 1.9 ± 0.1 | 60.0 ± 0.9 |
| 3-Methylpentane | 1.7 | 19.4 | 56.5 |
| | 1.9 | 19.6 | 63.9 |
| | 2.0 | 18.4 | 62.3 |
| | 1.5 | — | — |
| | 1.2 | — | — |
| MEAN + STD DEV: | 1.7 ± 0.3 | 19.2 ± 0.5 | 60.9 ± 3.8 |
| n-Hexane | 92.3 | 55.4 | 111.9 |
| | 90.1 | 54.5 | 105.4 |
| | 100.7 | 53.9 | 106.7 |
| | 99.3 | 56.7 | — |
| MEAN + STD DEV: | 95.6 ± 4.5 | 55.2 ± 1.0 | 107.9 ± 3.4 |

The sorption capacities are reported as weight gain in the sieve related to the dry weight of the pure zeolite. As shown in Table 2, the calcium-5A zeolite absorbed very little branched hydrocarbon. The ratio of 3-methylpentane/normal hexane sorption capacities is 0.018. In contrast, sodium ferrierite absorbed little dimethylbutane but adsorbed a substantial amount of 3-methylpentane. The ratio of the 3-methylpentane/normal hexane sorption capacity is about 20 times greater for the sodium ferrierite than for calcium-5A zeolite. The sodium ZSM-5 sieve absorbed virtually identical amounts of the mono- and di-branched isomers. Thus, the aforedescribed sodium ferrierite has the capability to effect a separation between 3-methylpentane and 2,3-dimethylbutane upstream of isomerization by capturing 3-methylpentane while permitting 2,3-dimethylbutane to elute and, thereby, has the capability to preserve the octane quality of the higher octane paraffin. Moreover, the sodium ferrierite treatment of a feed stream containing the aforementioned components will permit the capture (adsorption) of both 3-methyl-pentane and normal hexane which can then be desorbed and passed to an isomerization zone for their ultimate conversion to 2,3-dimethybutane.

EXAMPLE 2

The sorption capacities of hydrogen ferrierite towards the same three hydrocarbons were determined and are presented in Table 3. These data clearly show the comparison of the hydrogen ferrierite versus the calcium-5A zeolite. The ratio of 3-methylpentane/normal hexane sorption for the hydrogen ferrierite is about 25 times greater than that for the calcium-5A sieve. A comparison of the sodium ferrierite and hydrogen ferrierite, i.e., see Tables 2 and 3, underscores the discovery that appropriately sized molecular sieves can be very advantageous when placed upstream of an isomerization zone to separate out high octane hydrocarbons prior to isomerization.

TABLE 3

| Hydrocarbon | H-Ferrierite | Ca-5A |
|---|---|---|
| 2,3-Dimethylbutane | 3.6 | 1.6 |
| | 3.3 | 1.3 |
| | 3.2 | 1.9 |
| | 3.1 | 2.4 |
| MEAN + STD DEV: | 3.3 ± 0.2 | 1.8 ± 0.4 |
| 3-Methylpentane | 28.8 | 1.7 |
| | 28.6 | 1.9 |
| | 27.1 | 2.0 |
| | | 1.5 |
| | 27.4 | 1.2 |
| MEAN + STD DEV: | 28.0 ± 0.8 | 1.7 ± 0.3 |
| n-Hexane | 56.5 | 92.3 |

TABLE 3-continued

| Hydrocarbon | H-Ferrierite | Ca-5A |
|---|---|---|
|  |  | 90.1 |
|  |  | 100.7 |
|  |  | 99.3 |
| MEAN + STD DEV: | 56.5 | 95.6 ± 4.5 |

EXAMPLE 3

A sample of ammonium ferrierite was tableted to 14-45 mesh and placed in a glass tube. The glass tube was placed in a tube furnace under a flow of nitrogen and heated to 500° C. for 2 hours to expel ammonia and thus produce the hydrogen form of ferrierite. Under the same nitrogen flow, the molecular sieve was cooled to room temperature while the nitrogen flow was diverted through a gas saturation tower containing a mixture of normal hexane, 3-methylpentane and 2,3-dimethylbutane. The molecular sieves were exposed to hydrocarbon-containing streams of nitrogen for 1 hour. Samples of the hydrocarbon reservoir were taken at the beginning and at the end of the gas saturation period. The purpose of sampling both at the start and at the end of the experiment was to verify that the ratio of hydrocarbons remained essentially constant throughout the experiment. A portion of the hydrocarbon-containing vapor stream was diverted directly through a cold finger that was immersed in a dry ice/acetone bath to collect a sample of the actual hydrocarbon vapors.

Following exposure to these vapors, the hydrocarbon-saturated ferrierite sample was removed from the glass tube and placed on a vacuum line. The sample was evacuated to below 1 torr through a cold finger immersed in liquid nitrogen. The sample was heated to 40° C. and the sorbed hydrocarbon was quantitatively removed from the zeolite. It was experimentally determined that this first trapping was quantitative. The results of the adsorption were analyzed by gas chromatography and are shown in Table 4.

TABLE 4

Competitive Sorption of Hexane Isomers By H-Ferrierite

| Sample | % w 2,3-DMB | % w 3-MP | % w n-hexane |
|---|---|---|---|
| Gas saturation tower contents at start of experiment | 34.7 | 37.1 | 28.2 |
| Gas saturation tower contents at end of experiment | 26.7 | 36.8 | 36.5 |
| Gaseous hydrocarbon stream | 41.7 | 36.3 | 22.0 |
| Hydrocarbon adsorbed by H-ferrierite | 1.4 | 17.2 | 81.4 |

As shown in Table 4, very little dimethylbutane will enter the pores of the molecular sieve exemplified by hydrogen ferrierite. This is very advantageous because the higher octane dimethylbutane avoids capture (adsorption) and is thereby preserved upstream of isomerization A substantial amount of mono-methylpentane will be captured by the sieve and can then be recovered and passed to the isomerization zone for its conversion to 2,3-dimethyl-butane. Moreover, the unconverted or partially converted mono-methyl paraffins in the recycle stream (exemplified by conduit 125 in FIG. 2) can be readily isomerized to exhaustion in comparison to a process operated without the molecular sieve of the instant invention upstream of the isomerization zone.

What we claim as our invention is:

1. A process for the isomerization of paraffins from a first mixed hydrocarbon stream comprising normal paraffins, mono- methyl-branched paraffins, and di-methyl-branched paraffins, said process comprising:
    (a) passing said first mixed hydrocarbon stream to a first feed separation zone comprising a first shape-selective separatory molecular sieve having a pore size of 4.5×4.5A or smaller, said pore size being sufficient to permit entry of said normal paraffins but restrictive to prohibit entry of mono-methyl branched paraffins and di-methyl-branched paraffins and to produce a second mixed hydrocarbon stream comprising said mono-methyl branched paraffins and di-methyl branched paraffins and a first isomerization zone feed stream comprising normal paraffins;
    (b) passing said second mixed hydrocarbon stream of step (a) to a second feed separation zone comprising a second shape-selective separatory molecular sieve having a pore size intermediate 5.5×5.5 to 4.5×4.5A and excluding 4.5×4.5A, said pore size being sufficient to permit entry of normal paraffins and said mono-methyl-branched paraffins but restrictive to prohibit entry of di-methyl-branched paraffins;
    (c) separating, in said second feed separation zone, at separation conditions, by means of said second shape-selective separatory sieve, said di-methyl-branched paraffins from said mono-methyl-branched paraffins and producing a second feed separation zone effluent stream and a second isomerization zone feed stream;
    (d) recovering from said second feed separation zone a second feed separation zone effluent stream comprising said di-methyl-branched paraffins;
    (e) recovering from said first feed separation zone a first isomerization zone feed stream comprising said normal paraffins and recovering from said second feed separation zone a second isomerization zone feed stream comprising said mono-methyl branched paraffins;
    (f) passing at least a portion of said first, said second or both said first and second isomerization zone feed streams to an isomerization zone, maintained at isomerization conditions, and containing an isomerization catalyst to produce an isomerization zone effluent stream comprising di-methyl-branched paraffins, mono-methyl-branched paraffins and normal paraffins.

2. The process of claim 1 wherein at least a portion of said isomerization zone effluent stream is passed to a first product separation zone containing a select shape-selective molecular sieve to separate, at effluent stream separation conditions, said di-branched paraffins and said mono-methyl branched paraffins from said normal paraffins of said isomerization effluent stream and to form an isomerization zone recycle stream comprising normal paraffins; and recovering at least a portion of said di-methyl-branched paraffins and mono-methyl-branched paraffins as a first product separation zone effluent stream.

3. The process of claim 1 wherein said isomerization conditions include a temperature of 200° C. to 400° C. and a pressure of from about 10 bar to about 40 bar.

4. The process of claim 1 wherein said isomerization catalyst comprises an aluminosilicate having a Group VIII metal deposited therewith.

5. The process of claim 4 wherein said aluminosilicate is mordenite and said Group VIII metal is platinum.

6. The process of claim 5 wherein said platinum is present in a weight concentration of from about 0.2 to about 0.4 wt %.

7. The process of claim 5 wherein said mordenite has associated therewith an inorganic binder.

8. The process of claim 1 wherein said first shape-selective separatory molecular sieve comprises a calcium-5A molecular sieve.

9. The process of claim 1 wherein said second shape-selective separatory molecular sieve comprises a ferrierite molecular sieve.

10. The process of claim 1 wherein said second shape-selective separatory molecular sieve is selected from the group consisting of tectosilicates, aluminophosphates and silicoaluminophosphates molecular sieves.

11. The process of claim 10 wherein said tectosilicates are selected from the group consisting of aluminosilicates and borosilicates molecular sieves.

12. The process of claim 9 wherein said ferrierite molecular sieve has cations exchanged therewith selected from the group consisting of alkali metal, alkaline earth metal and transition metal cations.

13. The process of claim 1 wherein separation conditions maintained in said first mixed feed separation zone and said second mixed feed separation zones include a temperature of from about 75° C. to about 400° C. and a pressure of from about 2 bar to about 50 bar.

14. The process of claim 1 wherein said di-methyl-branched paraffins recovered in step (d) comprise 2,3-di-methylbutane and wherein said mono-methyl-branched paraffins recovered in step (e) comprise 3-methyl pentane.

15. The process of claim 2 wherein said first product separation zone effluent stream and said second feed separation zone effluent stream are admixed before blending with a gasoline range hydrocarbon.

16. The process of claim 1 wherein said second feed separation zone effluent stream and said isomerization zone effluent stream are combined and wherein said combined stream comprises an isomerate gasoline blending stream containing a predominant amount of di-methyl-branched paraffins and a minor amount of said mono-methyl-branched paraffins.

17. The process of claim 1 wherein said first and said second mixed hydrocarbon feed stream contains aromatic and naphthenic hydrocarbons and wherein said first and said second shape-selective separatory sieve are restrictive to prohibit entry of said aromatic and naphthenic hydrocarbons and wherein said aromatic and naphthenic hydrocarbons are recovered in said second feed separation zone effluent stream.

18. The process of claim 2 wherein said first product separation zone contains a calcium 5A zeolite sufficient to permit adsorption of said normal paraffins and restrictive to prevent adsorption of said mono-methyl-branched paraffins and di-branched paraffins.

19. The process of claim 2 wherein said first product separation zone effluent stream is passed to a second product separation zone containing a shape-selective molecular sieve to separate, at separation conditions, di-branched paraffins from mono-methyl branched paraffins and to form an isomerization zone recycle stream comprising mono-methyl branched paraffins and recovering at least a portion of said di-methyl-branched paraffins as a second product separation zone effluent stream .

20. The process of claim 19 wherein said select shape-selective molecular sieve of said second product separation zone has pore diameters between 4.5×4.5A to 5.5×5.5A and excluding 4.5×4.5A.

21. The process of claim 20 wherein said molecular sieve comprises ferrierite.

22. The process of claim 1 wherein at least a portion of said isomerization zone effluent stream is passed to a first isomerization product separation zone comprising a select shape-selective zeolite to separate, at separation conditions, said di-methy-branched paraffins from said mono-methyl branched paraffins and normal paraffins and to form an isomerization zone recycle stream comprising normal paraffins and mono-methyl branched paraffins; and recovering at least a portion of said di-methyl-branched paraffins.

23. The process of claim 22 wherein said select shape-selective zeolite of said first product separation zone has a pore diameter between 4.5×4.5A and 5.5×5.5A and excluding 4.5×4.5A.

24. The process of claim 22 wherein said shape-selective zeolite comprises a ferrierite molecular sieve.

25. The process of claim 1 wherein said isomerization zone effluent stream comprising di-methyl-branched paraffins and mono-methyl branched paraffins is separated by a separation means to provide a product effluent stream comprising di-methyl-branched paraffins and an isomerization zone recycle stream comprising mono-methyl branched paraffins.

26. The process of claim 1 wherein at least a portion of said isomerization zone effluent stream is recycled to said first and second feed separation zones.

27. The process of claim 1 wherein said isomerization zone effluent stream is separated to yield an isomerization zone recycle stream comprising normal paraffins which are recycled to said isomerization zone.

28. The process of claim 1 wherein said first isomerization zone feed stream of step (e) is passed to a first isomerization zone containing an isomerization catalyst to selectively isomerize normal paraffins to mono-methyl branched paraffins and di-methyl-branched paraffins.

29. The process of claim 28 wherein said first isomerization zone is maintained at conditions to maximize the production of di-methyl-branched paraffins.

30. The process of claim 29 wherein said second isomerization zone feed stream of step (e) is passed to a second isomerization zone containing an isomerization catalyst to selectively isomerize mono-methyl branched paraffins to di-methyl-branched paraffins.

31. The process of claim 30 wherein said second isomerization zone is maintained at conditions to maximize the production of di-methyl-branched paraffins.

32. The process of claim 28 wherein said di-methyl-branched paraffins comprise at least a portion of said first isomerization zone effluent stream and wherein said effluent stream is recycled to said first feed separation zone.

33. The process of claim 30 wherein said di-methyl-branched paraffins comprise at least a portion of said second isomerization zone effluent stream and wherein said effluent stream is recycled to said first feed separation zone.

34. A process for the isomerization of a hydrocarbon feed stream mixture containing normal hexane, mono-methyl pentanes and di-methyl butane which comprises: (1) passing said feed stream to a first feed separation zone containing a first separatory shape-selective molecular sieve having a pore size of 4.5 to 4.5A or smaller and being effective to adsorb said normal hexane and restrictive to prohibit entry of said mono-methyl pentanes and dimethyl butane and (2) passing said mono-methyl pentanes and di-methyl butane to a second feed separation zone containing a second separatory shape-selective molecular sieve having a pore size intermediate 5.5×5.5 to 4.5×4.5A and excluding 4.5×4.5A, said shape-selective molecular sieve being effective to permit entry of said mono-methylpentanes and restrictive to prohibit entry of said dimethyl butane and to thereby separate said dimethyl butane from said mono-methylpentanes; (3) recovering said dimethyl butanes as a first and second feed separation zone effluent stream; (4) recovering said adsorbed normal hexane from said first feed separation zone and adsorbed mono-methylpentanes from said second feed separation zone and passing said normal hexane and said mono-methylpentanes to an isomerization zone and isomerizing, at isomerization conditions in the presence of an isomerization catalyst, said normal hexane to methyl pentanes and dimethyl butane and said mono-methylpentanes to dimethyl butane, and 5forming an isomerization effluent isomerate stream comprising unisomerized normal hexane, mono-methylpentanes and dimethyl butane.

35. The process of claim 34 wherein at least a portion of said isomerization effluent isomerate stream is passed to a first product separation zone containing a third shape-selective separatory molecular sieve with a pore size equal to or smaller than 4.5×4.5A thereby permitting adsorption of said normal hexane while eluting said methylpentanes and said dimethylbutane, wherein said adsorbed normal hexane is recovered and at least a portion thereof is recycled to said isomerization zone and recovering said methyl pentanes and dimethyl butanes as a first product separation zone isomerate effluent.

36. The process of claim 34 wherein said second shape-selective molecular sieve is selected from the group consisting of tectosilicates, aluminophosphates and silicoaluminophosphates molecular sieves.

37. The process of claim 34 wherein said isomerate effluent comprising unreacted normal hexane, dimethylbutanes and mono-methylpentanes is passed to said first and second feed separation zones for product segregation.

38. The process of claim 36 wherein said tectosilicates comprise aluminosilicates and borosilicates molecular sieves.

39. The process of claim 38 wherein said aluminosilicate comprises ferrierite.

40. The process of claim 34 wherein said isomerization catalyst comprises a mordenite aluminosilicate having platinum dispersed thereon.

41. The process of claim 40 wherein said platinum is present in a weight content of from about 0.005 wt % to about 10.0 wt %.

42. The process of claim 34 wherein said isomerization catalyst comprises a Y faujausite sieve having 0.2 to 1.4 wt % platinum dispersed thereon.

43. The process of claim 34 wherein said feed stream is comprised of normal hexane, mono-methyl pentanes, dimethyl butane, aromatics and naphthenes, wherein said aromatics and naphthenes are not adsorbed in said first or said second separatory shape selective molecular sieve and wherein said aromatics and naphthenes elute with first and second feed separation zones effluent stream.

44. The process of claim 35 wherein said feed separation effluent stream comprising dimethyl butanes and said first product separation zone isomerate effluent comprising methyl pentanes and dimethyl butanes, are combined to form a combined isomerate gasoline blending component.

45. The process of claim 34 wherein said dimethyl butane is 2,3-dimethyl butane.

46. The process of claim 35 wherein said third shape-selective separatory molecular sieve in said first product separation zone comprises a calcium 5A zeolite.

47. The process of claim 34 wherein said first separatory shape selective molecular sieve comprises a calcium 5Å zeolite.

48. The process of claim 34 wherein said second separatory shape-selective molecular sieve comprises a ferrierite aluminosilicate.

49. The process of claim 35 wherein said first product separation zone isomerate effluent stream is passed to a second product separation zone containing a fourth select shape-selective molecular sieve to separate, at separation conditions, mono-methylpentanes from more highly branched paraffins comprising 2,3 dimethylbutane, to form an isomerization zone recycle stream comprising mono-methyl pentanes and wherein said more highly branched paraffins are recovered as a second product separation zone isomerate effluent stream.

50. The process of claim 49 wherein both said second feed separation zone and said second product separation zone contain a ferrierite aluminosilicate, wherein both said zones are maintained at separation conditions including a temperature of from about 75° C. to about 400° C. and a pressure of from about 2 bar to about 42 bar.

51. The process of claim 49 wherein said fourth select shape-selective molecular sieve of said second product separation zone has a pore diameter between 4.5×4.5A and 5.5×5.5A and excluding 4.5 to 4.5A.

52. The process of claim 34 wherein said effluent isomerate stream is combined with said first and said second feed separation zone effluent streams comprising dimethylbutane.

53. The process of claim 34 wherein said isomerization zone isomerate effluent stream comprises dimethylbutanes, mono-methylpentanes, and normal hexane, wherein at least a portion of said isomerization zone isomerate effluent stream is passed to said first and said second feed separation zones as a recycle stream.

54. The process of claim 34 wherein said isomerization zone effluent stream is separated to yield an isomerization zone recycle stream comprising normal hexane, wherein said normal hexane is passed to said isomerization zone to isomerize said normal hexane to mono-methylpentanes and dimethylbutane.

55. The process of claim 34 wherein said isomerization zone effluent stream is separated to produce an isomerization zone recycle stream comprising methylpentane, wherein said methylpentane is passed to said isomerization zone to isomerize said methylpentane to dimethylbutane.

* * * * *